US007732478B2

(12) United States Patent
Engebretson

(10) Patent No.: US 7,732,478 B2
(45) Date of Patent: Jun. 8, 2010

(54) METHODS FOR FACILITATING METABOLIC CONTROL

(75) Inventor: Steven P. Engebretson, New York, NY (US)

(73) Assignee: The Trustees of Columbia University in The City of New York, New York, NY (US)

( * ) Notice: Subject to any disclaimer, the term of this patent is extended or adjusted under 35 U.S.C. 154(b) by 1094 days.

(21) Appl. No.: 11/031,438

(22) Filed: Jan. 6, 2005

(65) Prior Publication Data

US 2005/0256197 A1 Nov. 17, 2005

(51) Int. Cl.
*A61K 31/40* (2006.01)
(52) U.S. Cl. .................... 514/414; 514/835; 514/866
(58) Field of Classification Search .............. 514/414, 514/835, 866
See application file for complete search history.

(56) References Cited

U.S. PATENT DOCUMENTS

| | | | |
|---|---|---|---|
| 5,464,609 A | 11/1995 | Kelm et al. | |
| 5,646,174 A | 7/1997 | Kelm et al. | |
| 5,785,951 A | 7/1998 | Kelm et al. | |
| 5,962,030 A * | 10/1999 | Fine | 424/646 |

FOREIGN PATENT DOCUMENTS

| | | | |
|---|---|---|---|
| EP | 0 519 983 B1 | 5/1996 | |
| WO | WO 2008042944 A2 * | 4/2008 | |

OTHER PUBLICATIONS

Brownlee et al., Advanced glycosylation end products in tissue and the biochemical basis of diabetic complications, N. Eng. J. Med., 318:1315-1321, 1988.
Morohoshi, M. et al., Glucose-dependent interleukin 6 and tumor necrosis factor production by human peripheral blood monocytes in vitro. Diabetes, 45:954-959, 1996.
Esposito, K. et al., Inflammatory cytokine concentrations are acutely increased by hyperglycemia in humans: Role of oxidative stress. Circulation, 106:2067-2072, 2002.
Schmidt, A.M. et al., Cellular receptors for advanced glycation end products. Arterioscler. Thromb., 14:1521-1528, 1994.
Fernandez-Real, J.M. et al., Insulin resistance and chronic cardiovascular inflammatory syndrome. Endocr. Rev., 24:278-301, 2003.
Duncan, B.B. et al., Factor VIII and other hemostasis variables are related to incident diabetes in adults. Diabetes Care, 22:767-772, 1999.
Cavanaugh, Jr., P.F. et al., Coordinate production of PGE2 and IL-1 beta in the gingival crevicular fluid of adults with periodontitis: its relationship to alveolar bone loss and disruption by twice daily treatment with ketorolac tromethamine oral rinse. J. Periodontal Res. 33:75-82, 1998.
Schmidt, A. M. et al., The multiligand receptor RAGE as a progression factor amplifying immune and inflammatory responses. J. Clin. Investigation, 108(7):949-955, 2001.
Bierhaus, A. et al., Diabetes-associated sustained activation of the transcription factor nuclear factor-kB. Diabetes, 50:2792-2808, 2001.
Cutler et al., Heightened gingival inflammation and attachment loss in type 2 diabetics with hyperlipidemia. J. Periodontal., 70: 1313-1321, 1999.
Engebretson et al., The Influence of interleukin gene polymorphism on expression of interleukin-1 beta and tumor necrosis factor alpha in periodontal tissue and gingival crevicular fluid. J. Periodontal, 70: 567-573, 1999.
Engebretson et al., GCF IL-1 beta profiles in periodontal disease. J. Clin. Peridontol., 29: 48-53, 2002.
Emrich et al., Periodontal disease in non-insulin-dependent diabetes mellitus. J. Periodontol., 62: 123-131, 1991.
Figueredo et al., Increased interleukin-1 beta concentration in gingival crevicular fluid as a characteristic of periodontitis. J. Periodontol., 70: 1457-1463, 1999.
Gowen and Mundy, Actions of recombinant interleukin 1, interleukin 2, and interferon-gamma on bone resorption in vitro. J. Immunol., 136: 2478-2482, 1986.
Hou et al., Crevicular Interleukin-1 beta in moderate and severe periodonitis patients and the effect of phase I periodontal treatment. J. Clin. Periodontol., 22: 162-67 1995.
Kurtis et al., IL-6 levels in gingival crevicular fluid (GCF) from patients with non-insulin dependent diabetes mellitus (NIDDM), adult periodontitis and healthy subjects. J. Oral Sci., 41: 163-167, 1999.
Lamster et al., A comparison of 4 methods of data presentation for lysosomal enzyme activity in gingival crevicular fluid. J. Clin. Periodontol., 15: 347-352, 1988.
Lamster et al., Correlation analysis for clinical and gingival crevicular fluid parameters at anatomically related gingival sites. J. Clin. Periodontol., 18: 272-277, 1991.
Losche et al., Plasma lipid and blood glucose levels in patients with destructive periodontal disease. J. Clin. Periodontol., 27: 537-541, 2000.
Masada et al., Measurement of interleukin-1 alpha and -1 beta in gingival crevicular fluid: implications for the pathogenesis of periodontal disease. J. Periodontal Res., 25: 156-163, 1990.
Mathur et al., Interleukin-1 alpha, interleukin-8 and interferon-alpha levels in gingival crevicular fluid. J. Periodontal Res., 31: 489-495, 1996.
Oliver and Tervonen, Periodontitis and tooth loss: comparing diabetics with the general population. J. Am. Dent. Assoc., 124: 71-76, 1993.
Oringer et al., Effect of locally delivered minocycline microspheres on markers of bone resorption. J. Periodontol., 73: 835-842, 2002.
Salvi et al., Inflammatory mediator response as a potential risk marker for periodontal diseases in insulin-dependent diabetes mellitus patients. J. Periodontol., 68: 127-135, 1997.

(Continued)

*Primary Examiner*—Kevin Weddington
(74) *Attorney, Agent, or Firm*—Bryan Cave LLP

(57) ABSTRACT

The present invention provides methods for facilitating metabolic control in a subject by decreasing the level of Il-1β in the GCF. The present invention further provides methods for decreasing the level of circulating TNF in a subject. Also provided are uses of anti-inflammatory agents in these methods.

6 Claims, 2 Drawing Sheets

OTHER PUBLICATIONS

Salvi et al., PGE2, IL-1 beta, and TNF-alpha responses in diabetics as modifiers of periodontal disease expression. Ann. Periodontol., 3: 40-50, 1998.

Schmidt et al., Advanced glycation endproducts (AGEs) induce oxidant stress in the gingival: a potential mechanism underlying accelerated periodontal disease associated with diabetes. J. Periodontal Res., 31:508-515, 1996.

Schmidt et al., Elevated plasma levels of vascular cell adhesion molecule-1 (VCAM-1) in diabetic patients with microalbuminuria: a marker of vascular dysfunction and progressive vascular disease. Br. J. Haematol., 92: 747-750, 1996.

Schmidt et al., RAGE: a novel cellular receptor for advanced glycation end products. Diabetes, 45: S77-S80, 1996.

Soskolne and Klinger, The relationship between periodontal diseases and diabetes: an overview. Ann. Periodontol., 6: 91-98, 2001.

Stashenko et al., Tissue levels of bone resorptive cytokines in periodontal disease. J. Periodontal., 62: 504-509, 1991.

Taylor et al., Severe periodontitis and risk for poor glycemic control in patients with non-insulin-dependent diabetes mellitus. J. Periondontol., 67: 1085-1093, 1996.

Taylor et al., Impact of oral diseases on systemic health in the elderly: diabetes mellitus and aspiration pneumonia. J. Public Health Dent., 60: 313-320, 2000.

Tervonen and Knuuttila, Relation of diabetes control to periodontal pocketing and alveolar bone level. Oral Surg. Oral Med. Oral Pathol., 61: 346-349. 1986.

Tervonen et al, Prevalence of periodontal pathogens with varying metabolic control of diabetes mellitus. J. Clin. Periodontol., 21: 375-379, 1994.

Tsai et al., Glycemic control of type 2 diabetes and severe periodontal disease in the US adult population. Community Dent. Oral Epidemiol., 30: 182-192, 2002.

Vlassara et al., Cachectin/TNF and IL-1 induced by glucose-modified proteins: role in normal tissue remodeling. Science, 240: 1546-1548, 1988.

Yan et al., Enhanced cellular oxidant stress by the interaction of advanced glycation end products with their receptors/binding proteins. J. Biol. Chem., 269: 9889-97, 1994.

Yuan et al., Detection of putative periodontal pathogens in non-insulin-dependent diabetes mellitus and non-diabetes mellitus by polymerase chain reaction. J. Periodontal Res., 36: 18-24, 2001.

Zambon et al., Microbiological and immunological studies of adult periodontitis in patients with noninsulin-dependent diabetes mellitus. J. Periodontol., 59: 23-31, 1988.

Al-Mubarak, et al., "Comparative evaluation of adjunctive oral irrigation in diabetics," J. Clin Periodontal 2002; 29: 295-300.

Ostrov, C.S. et al., "Keterolac, Prednisolone, and Dexamethasone for Postoperative Inflammation," Clin. Therapeut., 1997, vol. 19, No. 2, pp. 259-272.

Nishimura, F. et al., "Periodontal Inflammation and Insulin Resistance-Lessons from Obesity" J. Dent. Res., Aug. 2001, vol. 80, No. 8, pp. 1690-1694.

Grossi, S.G., "Treatment of Periodontal Disease and Control of Diabetes: An Assessment of the Evidence and Need for Future Research," Ann. Periodontol, Dec. 2001, vol. 6, No. 6, pp. 138-145.

* cited by examiner

Observed Frequencies for IL status post, A1c Status Post

|  | better | worse | Totals |
|---|---|---|---|
| ILLOWER | 16 | 7 | 23 |
| ILHIGHER | 1 | 6 | 7 |
| Totals | 17 | 13 | 30 |

Summary Table for A1c Status Post, TMT

| | |
|---|---|
| Num. Missing | 12 |
| DF | 2 |
| Chi Square | 6.473 |
| Chi Square P-Value | .0393 |
| G-Squared | 6.700 |
| G-Squared P-Value | .0351 |
| Contingency Coef. | .395 |
| Cramer's V | .430 |

FIG. 2

METHODS FOR FACILITATING METABOLIC CONTROL

The invention disclosed herein was made, at least in part, with U.S. Government support under Grant No. DE000449 from the National Institutes of Health. Accordingly, the U.S. Government has certain rights in this invention.

CROSS REFERENCE TO RELATED APPLICATIONS

The present application claims the benefit of U.S. application Ser. No. 10/754,181, filed Jan. 9, 2004, which is incorporated herein by reference thereto.

BACKGROUND OF THE INVENTION

Chronic periodontitis is a primary cause of tooth loss in adults. Periodontitis is normally caused by inflammation or infections of the gums (gingivitis), as well as the ligaments and bone that support the teeth. Loss of support causes the teeth to become loose and eventually fall out. The disease is also characterized by the presence of high levels of cytokines in the affected tissue of the gums.

Diabetes and hyperglycemia have been shown to have links to periodontal disease. For example, patients with type 2 diabetes have greater incidence and severity of periodontal disease than non-diabetics (Soskolne and Klinger, The relationship between periodontal diseases and diabetes: an overview. Ann. Periodontol., 6:91-98, 2001; Emrich et al., Periodontal disease in non-insulin-dependent diabetes mellitus. J. Periodontol., 62:123-31, 1991; Taylor et al., Impact of oral diseases on systemic health in the elderly: diabetes mellitus and aspiration pneumonia. J. Public Health Dent., 60:313-20, 2000; Oliver and Tervonen, Periodontitis and tooth loss: comparing diabetics with the general population. J. Am. Dent. Assoc., 124:71-76, 1993). A recent analysis of the National Health and Nutrition Examination Survey (NHANES) III data also showed that poor glycemic control in type 2 diabetes patients was associated with greater severity of periodontitis (Tsai et al., Glycemic control of type 2 diabetes and severe periodontal disease in the US adult population. Community Dent. Oral Epidemiol., 30:182-92, 2002). Furthermore, hyperglycemia has been thought to play a role in the incidence and prevalence of periodontal disease (Soskolne and Klinger, The relationship between periodontal diseases and diabetes: an overview. Ann. Periodontol., 6:91-98, 2001; Losche et al., Plasma lipid and blood glucose levels in patients with destructive periodontal disease. J. Clin. Periodontol., 27:537-41, 2000; Tervonen and Knuuttila, Relation of diabetes control to periodontal pocketing and alveolar bone level. Oral Surg. Oral Med. Oral Pathol., 61:346-49, 1986). Additionally, patients with relatively good glycemic control are less prone to periodontal destruction in longitudinal studies (Taylor et al., Severe periodontitis and risk for poor glycemic control in patients with non-insulin-dependent diabetes mellitus. J. Periodontol., 67:1085-93, 1996).

Early efforts to determine mechanisms that account for increased occurrence of periodontitis in diabetes mellitus focused on differences in the periodontal microflora. One report suggested that hyperglycemia was associated with an altered subgingival microbiota (Zambon et al., Microbiological and immunological studies of adult periodontitis in patients with noninsulin-dependent diabetes mellitus. J. Periodontol., 59:23-31, 1988). However, subsequent studies failed to identify differences in specific periodontal pathogens in diabetic versus non-diabetic subjects (Tervonen et al., Prevalence of periodontal pathogens with varying metabolic control of diabetes mellitus. J. Clin. Periodontol., 21:375-79, 1994; Yuan et al., Detection of putative periodontal pathogens in non-insulin-dependent diabetes mellitus and non-diabetes mellitus by polymerase chain reaction. J. Periodontal Res., 36:18-24, 2001).

Interleukin 1 (IL-1) is known to be a potent bone resorptive cytokine (Gowen and Mundy, Actions of recombinant interleukin 1, interleukin 2, and interferon-gamma on bone resorption in vitro. J. Immunol., 136:2478-82, 1986). Elevated levels of IL-1 in the gingival crevicular fluid (GCF) and gingival tissues have been associated with chronic periodontitis (Masada et al., Measurement of interleukin-1 alpha and -1 beta in gingival crevicular fluid: implications for the pathogenesis of periodontal disease. J. Periodontal Res., 25:156-63, 1990; Stashenko et al., Tissue levels of bone resorptive cytokines in periodontal disease. J. Periodontol., 62:504-09, 1991; Hou et al., Crevicular interleukin-1 beta in moderate and severe periodontitis patients and the effect of phase I periodontal treatment. J. Clin. Periodontol., 22:162-67, 1995; Mathur et al., Interleukin-1 alpha, interleukin-8 and interferon-alpha levels in gingival crevicular fluid. J. Periodontal Res., 31:489-95, 1996; Figueredo et al., Increased interleukin-1beta concentration in gingival crevicular fluid as a characteristic of periodontitis. J. Periodontol., 70:1457-63, 1999; Engebretson et al., The influence of interleukin gene polymorphism on expression of interleukin-1beta and tumor necrosis factor-alpha in periodontal tissue and gingival crevicular fluid. J. Periodontol., 70:567-73, 1999; Engebretson et al., GCF IL-1beta profiles in periodontal disease. J. Clin. Periodontol., 29:48-53, 2002). Several clinical studies have also demonstrated elevated inflammatory mediators, including IL-1, in the GCF of patients with type 1 diabetes, as compared with non-diabetic subjects (Kurtis et al., IL-6 levels in gingival crevicular fluid (GCF) from patients with non-insulin dependent diabetes mellitus (NIDDM), adult periodontitis and healthy subjects. J. Oral Sci., 41:163-67, 1999; Salvi et al., Inflammatory mediator response as a potential risk marker for periodontal diseases in insulin-dependent diabetes mellitus patients. J. Periodontol., 68:127-35, 1997; Salvi et al., PGE2, IL-1 beta, and TNF-alpha responses in diabetics as modifiers of periodontal disease expression. Ann. Periodontol., 3:40-50, 1998; Cutler et al., Heightened gingival inflammation and attachment loss in type 2 diabetics with hyperlipidemia. J. Periodontol., 70:1313-21, 1999).

Tumor necrosis factor (TNF) is a cytokine produced primarily by monocytes and macrophages. It, like other cytokines, is found in higher levels in people suffering from chronic periodontitis. TNF is also found in higher amounts within the plasma of patients with diabetes. Because TNF can adversely influence the insulin receptor and complicate glycemic control, it is desirable, from a diabetes-management perspective, to lower levels of TNF in a diabetes patient's circulation.

SUMMARY OF THE INVENTION

The present invention discloses methods for facilitating metabolic control in a subject. In one aspect, the present invention provides a method for facilitating metabolic control in a subject by decreasing the level of IL-1β in GCF of the subject. Also provided is a use of an anti-inflammatory agent in this method. The subject may have type 2 diabetes, hyperglycemia, and periodontitis.

In another aspect, the present invention provides a method for facilitating metabolic control in a subject, by decreasing the level of IL-1β in GCF of the subject, such that the level of circulating TNF is decreased in the subject. Also provided is a use of an anti-inflammatory agent in this method.

In still another aspect, the present invention provides a method for decreasing the level of circulating TNF in a subject, by decreasing the level of IL-1β in GCF of the subject. Also provided is a use of an anti-inflammatory agent in this method.

Additional aspects of the present invention will be apparent in view of the description which follows.

BRIEF DESCRIPTION OF THE FIGURES

FIG. 2 depicts the effect of lowing GCF IL-1 by operation on the level of HbA1c. 30 subjects were treated as in FIG. 1. Subjects whose IL-1 was lowered over three months had lowered HbA1c (a measure of long term glucose control). This result was statistically significant (p=0.039).

DETAILED DESCRIPTION OF THE INVENTION

Figure 1:
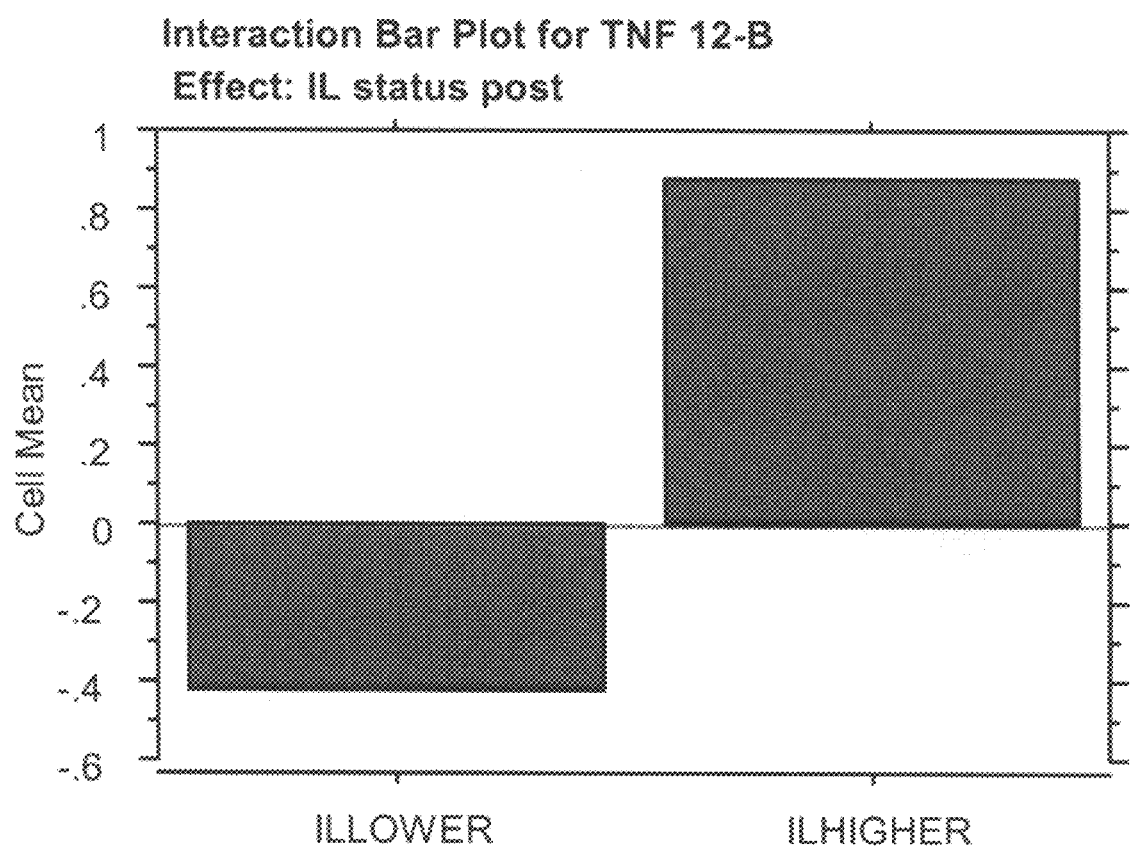
FIG. 1 depicts the effect of lowing GCF IL-1 by operation on the level of circulating TNF. 28 subjects with chronic periodontitis and type 2 diabetes were treated with scaling and root planing and followed for three months. This figure shows the mean plasma TNF change among those whose IL-1 was lowered (n=21) during the study compared with those whose IL-1 went higher (n=7) during the study.

Patients with diabetes have increased incidence and severity of periodontal disease not accounted for by differences in the subgingival microbial infection. Poor glycemic control has been consistently associated with periodontal disease severity. Although evidence suggests that hyperglycemia may induce inflammatory cytokine production, few studies, however, have examined the systemic effects of local periodontal inflammation in patients with type 2 diabetes.

As disclosed herein, the present invention shows that hyperglycemia is associated with high GCF levels of IL-1 and high circulating TNF levels in patients with type 2 diabetes and chronic periodontitis. Although it is known in the art that the level of IL-1β in the GCF of type 1 diabetes patients is significantly-elevated, the present invention is the first to demonstrate the correlation between GCF IL-1β and hyperglycemic control (Salvi et al., Inflammatory mediator response as a potential risk marker for periodontal diseases in insulin-dependent diabetes mellitus patients. *J. Periodontol.*, 68:127-35, 1997).

It is generally believed that a hyperresponsive monocytic mechanism is responsible for elevated cytokine levels found in type 1 diabetes patients (Salvi et al., Inflammatory mediator response as a potential risk marker for periodontal diseases in insulin-dependent diabetes mellitus patients. *J. Periodontol.*, 68:127-35, 1997; Salvi et al., PGE2, IL-1 beta, and TNF-alpha responses in diabetics as modifiers of periodontal disease expression. *Ann. Periodontol.*, 3:40-50, 1998). The theory suggests that a heightened inflammatory response, either because of gene polymorphism or hyperglycemia, causes a heightened monocyte release of inflammatory mediators.

Other factors, such as elevated glucose levels in a diabetes patient, may also directly or indirectly lead to a heightened inflammatory response. A mechanism to account for this finding involves the non-enzymatic glycation of tissue proteins and the production of advanced glycation end products (AGEs) (Brownlee et al., Advanced glycosylation end products in tissue and the biochemical basis of diabetic complications. *N. Engl. J. Med.*, 318:1315-21, 1988). Hyperglycemia results in reversible and irreversible changes to the host, including formation of glycated proteins called AGEs. Receptors for AGEs (RAGEs) have been identified. AGE formation, and AGE-RAGE interaction at the cell surface of endothelial cells and mononuclear phagocytes, have been shown to generate reactive oxygen intermediates and enhance the expression of pro-inflammatory cytokines through a mechanism involving the nuclear transcription factor kappa B (NFκB) (Yan et al., Enhanced cellular oxidant stress by the interaction of advanced glycation end products with their receptors/binding proteins. *J. Biol. Chem.*, 269:9889-97, 1994; Schmidt et al., The multiligand receptor RAGE as a progression factor amplifying immune and inflammatory responses. *Diabetes*, 50:2792-808, 2001). AGE-RAGE interactions have been shown in vitro to upregulate NFκB-associated gene products, which include vascular cell adhesion molecules and proinflammatory cytokines (Vlassara et al., Cachectin/TNF and IL-1 induced by glucose-modified proteins: role in normal tissue remodeling. *Science*, 240:1546-48, 1988; Yan et al., Enhanced cellular oxidant stress by the interaction of advanced glycation end products with their receptors/binding proteins. *J. Biol. Chem.*, 269:9889-97, 1994; Schmidt et al., Elevated plasma levels of vascular cell adhesion molecule-1 (VCAM-1) in diabetic patients with microalbuminuria: a marker of vascular dysfunction and progressive vascular disease. *Br. J. Haematol.*, 92:747-50, 1996). RAGE is present in the gingival tissues, and has been linked to oxidative stress (Schmidt et al., Advanced glycation endproducts (AGEs) induce oxidant stress in the gingiva: a potential mechanism underlying accelerated periodontal disease associated with diabetes. *J. Periodontal Res.*, 31:508-15, 1996). Furthermore, since RAGE receptors are present on mononuclear phagocytes, AGE-RAGE interactions in diabetic tissues may account for a heightened inflammatory response (Schmidt et al., RAGE: a novel cellular receptor for advanced glycation end products. *Diabetes*, 45:S77-S80, 1996; Schmidt et al., The multiligand receptor RAGE as a progression factor amplifying immune and inflammatory responses. *Diabetes*, 50:2792-808, 2001).

Other cytokines are also likely to play a role in the increased incidence and severity of periodontal disease in patients with type 2 diabetes. Tumor necrosis factor (TNF) has been found to be present in higher amounts within the blood plasma of patients with diabetes. It has been previously thought that adipocytes associated with obesity were the major source of circulating TNF. Thus, it was believed that weight loss would contribute, in part, to lower circulating TNF levels. Historically, however, the control of obesity in patients with diabetes has been extremely difficult.

The present invention has now shown that chronic periodontitis is also a significant contributor to circulating TNF. In particular, the present invention has demonstrated that, by lowering GCF IL-1β in diabetes patients with chronic periodontitis—either by operation or with an adjunctive rinse or both—circulating TNF levels is lowered, and insulin resistance is significantly reduced; thus, a more desirable level of glycemic control (as measured by HbA1c) is achieved. Additionally, the present invention discloses that GCF IL-1β is associated with elevated levels of circulating TNF. Studies performed by the inventor have shown that a reduction in IL-1β in the GCF reduce circulating TNF. In clinical trials, those subjects whose IL-1β levels were decreased as a result of therapy had decreased TNF levels. Moreover, those subjects with lowered TNF levels also had improved glucose control. Since TNF interferes with the insulin receptor, and, as a consequence, with glucose metabolism, a decrease in TNF restores the function of the insulin receptor and improve glucose metabolism in a subject, particularly, a diabetes patient.

As described herein, the inventor has determined that increasing IL-1β levels in the GCF contributes to the rise of circulating TNF levels. The levels of IL-1β in the GCF may be lowered by operations, such as scaling and root planing (SRP), the standard chronic periodontitis treatment. Ketorolac, a non-steroidal anti-inflammatory drug, has also been shown to reduce GCF IL-1β in the oral cavity when used as an oral rinse. Accordingly, Ketorolac oral rinse (KOR) may also be useful in the management of diabetes patients.

In view of the foregoing, the present invention provides a method for facilitating (e.g., improving, assisting) metabolic control in a subject. Control over any aspect of metabolism may be facilitated in accordance with this method. In a preferred embodiment, control over glucose metabolism is facilitated. Metabolic control of glucose may be assessed in the subject, for example, by measuring the levels of HbA1c in the subject, as described herein, where a decrease in the level of HbA1c reflects improved control over glucose metabolism.

In accordance with the present invention, the method for facilitating metabolic control in a subject comprises decreasing the level of IL-1β in GCF of the subject. In one embodiment, metabolic control is facilitated in the subject by decreasing the level of circulating TNF in the subject. As used herein, "circulating TNF" refers to systemic TNF, or TNF that is not localized to a particular part of the body of the subject. For example, the level of circulating TNF in a subject may be determined by measuring the level of TNF in the subject's blood.

The subject of the present invention may be any animal, including amphibians, birds, fish, mammals, and marsupials, but is preferably a mammal (e.g., a human; a domestic animal, such as a cat, dog, monkey, mouse, and rat; or a commercial animal, such as a cow or pig). In one embodiment, the subject has diabetes. As used herein, "diabetes" is a general term that refers to disorders characterized by excessive urine excretion (polyuria). Examples of diabetes include, without limitation, brittle diabetes (labile diabetes, unstable diabetes), bronze diabetes (hemochromatosis), diabetes insipidus (water diabetes), gestational diabetes, insulin-dependent diabetes mellitus (IDDM, type I diabetes, juvenile diabetes, juvenile-onset diabetes), and noninsulin-dependent diabetes mellitus (NIDDM, adult-onset diabetes, type II diabetes). Also within the scope of the present invention is impaired glucose tolerance (IGT, borderline diabetes, chemical diabetes, latent diabetes, subclinical diabetes). In another embodiment of the present invention, the subject has hyperglycemia. A subject has hyperglycemia when his/her level of glucose (sugar) in the blood is above normal.

As used herein, the term "periodontitis" includes any dental disorder that results from progression of gingivitis, involving inflammation and infection of the ligaments and bones that support the teeth. Examples of periodontitis include, without limitation, acute periodontitis, chronic periodontitis, pyorrhea gum disease, severe gum disease, and severe gum inflammation.

In accordance with the method of the present invention, the level of IL-1β in GCF of the subject may be decreased using an anti-inflammatory agent. The anti-inflammatory agent of the present invention may be any agent that acts against, counters, decreases, diminishes, inhibits, or reduces inflammation or an inflammatory response. The agent may be any protein, polypeptide, peptide, nucleic acid (including DNA or RNA), antibody, Fab fragment, F(ab')$^2$ fragment, molecule, antibiotic, drug, compound, or any combination thereof. The agent may also be a pharmaceutical composition comprising any of the foregoing, or combination thereof, and a pharmaceutically-acceptable carrier. The pharmaceutically acceptable carrier must be "acceptable" in the sense of being compatible with the other ingredients of the composition, and not deleterious to the recipient thereof. The pharmaceutically-acceptable carrier employed herein is selected from various organic or inorganic materials that are used as materials for pharmaceutical formulations, and which may be incorporated as analgesic agents, buffers, binders, disintegrants, diluents, emulsifiers, excipients, extenders, glidants, solubilizers, stabilizers, suspending agents, tonicity agents, vehicles, and viscosity-increasing agents. If necessary, pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc, and water, among others.

The pharmaceutical composition of the present invention may be prepared by methods well-known in the pharmaceutical arts. For example, the composition may be brought into association with a carrier or diluent, as a suspension or solution. Optionally, one or more accessory ingredients (e.g., buffers, flavoring agents, surface active agents, and the like) also may be added. The choice of carrier will depend upon the route of administration of the formulation. Formulations of the composition may be conveniently presented in unit dosage, or in such dosage forms as aerosols, capsules, elixirs, emulsions, injections, liquid drugs, pills, powders, granules, suspensions, syrup, tablets, or troches, which can be administered orally, topically, or by injection (e.g., intravenous, intraperitoneal, subcutaneous, and intramuscular injection), but is preferably administered orally.

In one embodiment of the present invention, the agent is a pharmaceutical composition comprising an anti-inflammatory compound in solution (i.e., in the form of a rinse). By way of example, the anti-inflammatory rinse may be a ketorolac oral rinse. Ketorolac (also known as Acular® and Toradol®) is a commercially-available pyrrolo-pyrrole non-steroidal anti-inflammatory agent with antipyretic and analgesic properties. It is similar in action to ibuprofen, but is substantially more potent and capable of relieving severe pain. The formulation and composition of ketorolac oral rinse are fully described in U.S. Pat. Nos. 5,464,609, 5,646,174, and 5,785,951, and European Patent EP 0519983 B1, the contents of which are hereby incorporated by reference herein.

The anti-inflammatory agent of the present invention is used in an amount effective to decrease the level of IL-1β in GCF of the subject. The level of IL-1β in the GCF of the subject may be measured by standard techniques and assays, including those described herein. On this basis, the effective amount of anti-inflammatory agent may be determined by the skilled artisan. The effective amount of anti-inflammatory agent is also expected to facilitate metabolic control in the subject. For example, where the subject has a metabolic disorder, the effective amount of anti-inflammatory agent may provide an increased amount of glucose control to the subject, and may even be effective to ameliorate or minimize the clinical impairment or symptoms resulting from the metabolic disorder. For example, where the metabolic disorder is hyperglycemia, the clinical impairment or symptoms of the disorder may be ameliorated or minimized by diminishing thirst, improving dry mouth, and diminishing the need to urinate often. The amount of anti-inflammatory agent that is effective to facilitate metabolic control in a subject will vary, depending on the particular factors of each case, including the type of metabolic disorder, the stage of the disorder, the subject's weight, the severity of the subject's condition, and the method of administration. These amounts can be readily determined by the skilled artisan.

In the method of the present invention, the level of IL-1β in the GCF of a subject also may be decreased by way of an operation—either alone or in combination with the anti-inflammatory agent. As used herein, an "operation" includes any methodical action of the hand, or instruments, on the human body, to produce a curative or remedial effect, to repair damage, and/or to restore health. For example, the operation may be a surgical procedure, such as debridement (the surgical excision of dead or dying tissue, which may have poor or no circulation, and which may become infected), e.g., by SRP. Root planing, as part of periodontal therapy, is a procedure for smoothing out the roughened root surface or cementum of a tooth, often following subgingival curettage or ultrasonic scaling (including fine scaling and gross scaling). SRP is generally performed to remove calculus and halt periodontal disease progression within the pocket environment. The SRP of the present invention may be any kind of SRP procedure, including, without limitation, use of instruments on a quadrant basis (quadrant SRP) and full-mouth SRP.

The present invention further provides a method for facilitating metabolic control in a subject, by decreasing the level of IL-1β in GCF of the subject, such that the level of circulating TNF is decreased in the subject. In one embodiment, the metabolic control is glucose control. The subject may be any of those described above. In one preferred embodiment, the subject has diabetes (e.g., type 2 diabetes); in another preferred embodiment, the subject has hyperglycemia. By way of example, the level of IL-1β in GCF of the subject may decreased using an anti-inflammatory agent (e.g., a rinse, such as ketorolac oral rinse), an operation (e.g., SRP), or both.

The present invention also provides a method for decreasing the level of circulating TNF in a subject, by decreasing the level of IL-1β in GCF of the subject. In one embodiment, metabolic control in the subject is facilitated by decreasing the level of circulating TNF in the subject.

In view of the foregoing, the present invention further provides use of an anti-inflammatory agent in a method for facilitating metabolic control in a subject by decreasing the level of IL-1β in GCF of the subject. Additionally, the present invention provides use of an anti-inflammatory agent in a method for facilitating metabolic control in a subject by decreasing the level of circulating TNF in the subject. The present invention also provides use of an anti-inflammatory agent in a method for decreasing the level of circulating TNF in a subject by decreasing the level of IL-1β in GCF of the subject.

The present invention is described in the following Examples, which are set forth to aid in the understanding of the invention, and should not be construed to limit in any way the scope of the invention as defined in the claims which follow thereafter.

EXAMPLES

Example 1

Patient Selection

The patient population of this study consisted of 45 adult patients recruited from an outpatient diabetes center (Naomi Berrie Diabetes Center, Columbia University Health Sciences Center, New York, N.Y., USA) during routine medical-care visits. All subjects were diagnosed with type 2 diabetes at least six months previously, using standard World Health Organization (WHO) criteria, and were being treated with stable doses of oral hypoglycemic agents and/or insulin. For entry to the study, patients also required a diagnosis of chronic periodontitis for which non-surgical treatment was indicated. An intraoral radiographic series was used to confirm this diagnosis. Exclusion criteria included pregnancy or lactation, HIV infection, bleeding disorders, and immunosuppressive chemotherapy.

The study was approved by the Institutional Review Board at Columbia University Health Sciences Center, and written informed consent was obtained from all patients.

Example 2

Study Subjects

The subjects in this study were approximately evenly divided between male and female, and tended to be older adults with a mean age of 54. Almost all had long-standing diabetes (mean number of years since diabetes diagnosis=9.1). Other demographic and clinical parameters of the individuals in this study (mean±standard deviation) are provided in Table 1.

TABLE 1

| Characteristics (mean ± SD, range) of the study population | | |
|---|---|---|
| Number of Subjects | 45 | |
| Age | 54.0 ± 9.8 | 32-69 |
| Gender (% female) | 55% | |
| Mean probing depth (mm) | 3.35 ± 0.79 | 2.27-5.31 |
| Probing depth of the sampled site (mm) | 4.27 ± 0.97 | 2.63-7.63 |
| Mean clinical attachment loss (mm) | 4.05 ± 1.27 | 2.48-7.62 |
| % Plaque | 77.2 ± 23.0 | 14.6-100 |
| % BOP | 55.9 ± 27.1 | 12.8-100 |
| HbA1c (%) | 7.82 ± 1.96 | 4.7-12.0 |
| Time since diagnosis of diabetes (years) | 9.08 ± 9.49 | 0.5-48.0 |

Example 3

GCF Collection

The clinical evaluation was preceded by collection of GCF, as previously described (Lamster et al., A comparison of 4 methods of data presentation for lysosomal enzyme activity in gingival crevicular fluid. *J. Clin. Periodontol.*, 15:347-52, 1988; Lamster et al., Correlation analysis for clinical and gingival crevicular fluid parameters at anatomically related gingival sites. *J. Clin. Periodontol.*, 18:272-77, 1991), from the mesiolingual and mesiobuccal surfaces of the first molar tooth in each quadrant. Where the first molar was absent, the second molar was sampled. If both the first and second molar were missing, the second premolar was sampled. If there were no posterior teeth in a quadrant, no sample was taken from that quadrant.

Briefly, teeth were air-dried and isolated with cotton rolls, supragingival plaque was gently removed, and GCF was sampled with precut methylcellulose filter paper strips for 30 sec. Strips were measured for fluid volume with a calibrated Periotron 6000 (Interstate Drug Exchange, Amityville, N.Y.), then removed to separate microcentrifuge tubes containing 50 μl of phosphate-buffered saline (Tween 20). The tubes were stored at −20° C. until eluted (maximum 48 h). Following elution, each GCF sample was analyzed separately.

It is known that the way sampling is conducted significantly affects experimental results and the reliability of the results. The present study was designed to sample predetermined anatomic locations within the periodontium, rather than the most inflamed sites or deepest sites. Shallow, medium, and deep probing depths were involved in this study, so that sites of clinically-different characteristics could be compared. Sampling of only inflamed or deepest sites may give an inaccurate profile of inflammatory mediators, since probing depth and clinical inflammation are strongly associated with the level of IL-1β (Engebretson et al., GCF IL-1beta profiles in periodontal disease. *J. Clin. Periodontol.,* 29:48-53, 2002; Oringer et al., Effect of locally delivered minocycline microspheres on markers of bone resorption. *J. Periodontol.,* 73:835-42, 2002). Any description of inflammatory mediators in the GCF from diseased periodontium should, therefore, consider the probing depth of the sampled site.

Example 4

Clinical Measures

Clinical data included probing depth (PD), attachment level (AL), plaque index (PI), and bleeding on probing (BOP), and were collected at six sites per tooth. PD (manually determined) was defined as the distance in millimeters from the coronal-most margin of the free gingiva to the most apical penetration of the North Carolina probe. AL was defined as the distance from the cemento-enamel junction to the most apical penetration of the probe. The presence of supragingival plaque was recorded dichotomously during PD measurements. Bleeding on probing (BOP) within 20 sec was recorded dichotomously.

Example 5

Analysis of IL-1β in GCF

GCF samples were analyzed for IL-1β using a commercially-available enzyme-linked immunosorbant assay, Multikine Kit (Cistron Biotechnology, Pine Brook, N.J.). This assay is a sandwich ELISA; it was performed according to manufacturer's instructions using human recombinant standards. Results were reported as total amount of IL-1β (in pg±SD) per 30-sec sample, as described previously (Engebretson et al., The influence of interleukin gene polymorphism on expression of interleukin-1beta and tumor necrosis factor-alpha in periodontal tissue and gingival crevicular fluid. *J. Periodontol.,* 70:567-73, 1999), and expressed as pg/sample. Where IL-1 levels were compared between patient groups, mean whole-mouth values were used.

Example 6

Analysis of HbA1c

Glycated hemoglobin (HbA1c) levels were measured from freshly drawn anticoagulated whole blood using an automated affinity chromatography system (BioRad Micromat II, Hercules, Calif.). Serum glucose was determined by the glucose oxidase method (Roche Diagnostics, Basel, CH). Since subjects were seen at various times throughout the day, these are random glucose samples.

Example 7

Statistical Analysis

Since GCF IL-1β it is not normally distributed, Spearman correlation was used to calculate correlation coefficients between mean patient GCF IL-1β and PD, AL, BOP, plaque, HbA1c, and serum glucose. In order to compare the GCF IL-1β levels of groups of different glycemic control, the inventor dichotomized subjects based on HbA1c values greater than or less than 8%, and used the Mann-Whitney U test to compare non-normally-distributed continuous variables. The association of GCF IL-1β with hyperglycemia was also evaluated by multivariate logistic regression analysis. Adjustments were made for clinical periodontal parameters and other pertinent variables (age, sex, HbA1c). The dependent variable, IL-1β, was categorized as being greater than or equal to the median value (ln(IL-1β)>50%). Adjusted odds ratios and 95% confidence interval were also calculated. All analyses were performed with the use of the Statview statistical package (SAS Institute, Cary, N.C.), version 5.0.

Discussed below are results obtained by the inventor in connection with the experiments of Examples 1-7:

A total of 176 GCF samples were collected. The inventor's study design called for the collection of samples from each of four first-molar sites. Because of missing teeth, the resulting samples collected by the inventor were as follows: 4 samples from 42 subjects; 3 samples from 2 subjects; and 2 samples from 1 subject. GCF levels of IL-1β demonstrated a significant positive correlation with mean probing depth (r=0.613, P<0.0001), mean clinical attachment loss (r=0.587, P=0.0001), percentage of sites exhibiting bleeding on probing (% BOP) (r=0.424, P=0.006), % HbA1c (r=0.371, P=0.01), and random serum glucose (r=0.490, P=0.002), but not percentage of sites exhibiting plaque (% plaque) (r=0.231, P=0.14). The inventor then compared patients according to their relative glycemic control using the Mann-Whitney U test.

Table 2 illustrates the results when HbA1c was categorized as less than or equal to 8%, or greater than 8%. Total amounts of GCF IL-1β were significantly higher in those with greater than 8% HbA1c (P=0.01), while only a trend (P=0.14) was seen for GCF concentrations of GCF IL-1.

TABLE 2

A comparison of mean (±standard deviation) patient GCF IL-1β levels in total amount (pg/sample) and concentration (pg/μl), stratified by glycemic control status (8%) by Mann-Whitney U Test. *P < .05

|  | GCF IL-1β pg/sample | GCF IL-1β pg/μl |
|---|---|---|
| All Subjects | 77.9 ± 54.0 | 78.7 ± 66.5 |
| HbA1c less than 8% | 61.8 ± 50.3 | 76.7 ± 82.5 |
| HbA1c greater than 8% | 99.2 ± 52.4* | 81.3 ± 38.2* |

TABLE 3

A Comparison of Median (interquartile range) Patient GCF IL-1β Levels in Total Amount (pg/sample) and Concentration (pg/μl), by Glycemic Control Status

|  | GCF IL-1β pg/sample | GCF IL-1β pg/μl |
|---|---|---|
| All Subjects | 70.2 (33.2-107.2) | 67.0 (40.7-93.3) |
| HbA1c ≤ 8% | 49.1 (18.3-80) | 55.8 (32.3-79.3) |
| HbA1c > 8% | 89.0 (61.7-116.3)* | 77.6 (54.7-100.5)* |

*P = .01

TABLE 4

Multivariate Model, Using Median GCF IL-1β (Table 3) as the Dependent Variable (Ln(IL-1) > 50%). HbA1c remained a significant predictor of GCF IL-1β, after adjusting for AL, BOP, PI, age, and gender.
Logistic Model Coefficients Table for Ln(IL-1) > 50% CAT

|  | Coefficient | Odds Ratio | 95% Confidence Interval | P Value |
| --- | --- | --- | --- | --- |
| Ln(IL-1) > 50% | 2.23 | 4.47 | 1.21-16.53 | .0246 |
| Mean AL |  |  |  |  |
| % BOP | -.997 | 0.09 | 0.001-9.65 | .3170 |
| % Plaque | .959 | 7.6 | 0.12-471.25 | .3369 |
| HbA1c | 2.69 | 2.19 | 1.24-3.87 | .0071 |
| AGE | .170 | 1.008 | 0.919-1.106 | .8586 |
| Female Gender | .700 | 1.78 | 0.352-9.031 | .4846 |

In a multivariate model, using above-median GCF IL-1β as the dependent variable, HbA1c remained a significant predictor of GCF IL-1β, after adjusting for AL, BOP, PI, age, and gender (adjusted odds ratio (OR), 2.19; 95% CI, 1.24 to 3.87) (Table 4). When probing-depth of the sampled site was used as an independent variable in place of AL, HbA1c remained a significant predictor of GCF IL-1β (adjusted OR, 1.79; 95% CI, 1.09 to 2.94). Random serum glucose was substituted for HbA1c in the multivariate model; similarly, it was associated with above-median GCF IL-1β (adjusted OR, 1.02; 95% CI, 1.007 to 1.039), but not as strongly as HbA1c.

Based upon these data, it was determined that clinical periodontal measures (PD, AL, BOP) and measures of glycemic control (HbA1c and random glucose) were significantly correlated with GCF IL-1β. In particular, patients with greater than 8% HbA1c had significantly higher mean GCF IL-1 levels than patients with less than 8% HbA1c. In a multivariate model adjusting for age, gender, PD, AL, BOP, and PI, HbA1c and random glucose were independent predictors of high GCF IL-1β. These data indicate that hyperglycemia contributes to a heightened inflammatory response, and poor glycemic control is associated with elevated GCF IL-1β and causes periodontal destruction.

These data further indicate that hyperglycemia was a significant contributor to GCF IL-1β, even when periodontal clinical measures were included in the multivariate model. Furthermore, glycemia levels were positively associated with GCF IL-1β, regardless of whether the glucose measurement reflected the actual blood level at the time of GCF sampling (random serum glucose) or the longer term measure of glycemic control (HbA1c). While both measures were significant predictors of GCF IL-1β, HbA1c was a much stronger predictor of GCF IL-1β than random glucose.

This study found that hyperglycemia is independently associated with high GCF levels of IL-1β in patients with type 2 diabetes and chronic periodontitis. Previous studies (Hou, L. T. et al., Crevicular interleukin-1 beta in moderate and severe periodontitis patients and the effect of phase I periodontal treatment. J. Clin. Periodontol, 22:162-167, 1995; Figueredo, C. M. et al., Increased interleukin-1β concentration in gingival crevicular fluid as a characteristic of periodontitis. J. Periodontol, 70:1457-1463, 1999; Engebretson, S. P et al., GCF IL-1beta profiles in periodontal disease. J. Clin. Periodontol, 29:48-53, 2002; Engebretson, S. P. et al., The influence of interleukin gene polymorphism on expression of interleukin-1β and tumor necrosis factor-a in periodontal tissue and gingival crevicular fluid. J. Periodontol, 70:567-573, 1999) have shown that IL-1β is strongly related to periodontal clinical parameters, particularly probing depth of the sampled site. Nonetheless, in this study even when including periodontal clinical measures in the multivariate model, hyperglycemia was a significant contributor to GCF IL-1β. Also, glycemia levels were positively associated with GCF IL-1β regardless of whether the glucose measurement reflected the actual blood level at the time of GCF sampling (random serum glucose) or the longer-term measure of glycemic control, HbA1c. While both measures were significant predictors of GCF IL-1β, HbA1c was a much stronger predictor of GCF IL-1β than random glucose. These results suggest an altered host response to microbial infection in diabetic subjects mediated, at least in part, by hyperglycemia.

Hyperglycemia has been thought to play a role in periodontal disease incidence and prevalence (Soskolne W. A. et al., The relationship between periodontal diseases and diabetes: An overview. Ann. Periodontol, 6:91-98, 2001; Losche, W. et al., Plasma lipid and blood glucose levels in patients with destructive periodontal disease. J. Clin. Periodontol, 27:537-541, 2000; Tervonen, T. et al., Relation of diabetes control to periodontal pocketing and alveolar bone level. Oral Surg. Oral Med. Oral Pathol., 61:346-349, 1986). It has been found that patients with relatively good glycemic control are less prone to periodontal destruction in longitudinal studies (Taylor, G. W. et al., Severe periodontitis and risk for poor glycemic control in patients with non-insulin-dependent diabetes mellitus. J. Periodontol, 67:1085-1093, 1996). Recent analysis of the NHANES III data showed that worse glycemic control in type 2 diabetes patients was associated with more severe periodontitis (Tsai C. et al., Glycemic control of type 2 diabetes and severe periodontal disease in the US adult population. Community Dent. Oral Epidemiol, 30:182-192, 200). The findings of the current study are consistent with these reports.

The finding of elevated IL-1β in the GCF of patients with type 2 diabetes and poor glycemic control is consistent with a previous study of type 1 diabetes by Salvi et al. (Salvi, G. E. et al., Inflammatory mediator response as a potential risk marker for periodontal diseases in insulin-dependent diabetes mellitus patients. J. Periodontol, 68:127-135, 1997) In that study, significantly elevated IL-1β and prostaglandin $E_2$ levels were found in the GCF of patients with diabetes compared with non-diabetic control subjects regardless of periodontal disease severity. However, that study did not find a correlation between GCF IL-1 and HbA1c, which is inconsistent with this study. These results are also consistent with those of Cutler et al. (Cutler, C. W. et al., Heightened gingival inflammation and attachment loss in type 2 diabetics with hyperlipidemia. J. Periodontol, 70:1313-1321, 1999) who showed a trend for increased GCF IL-1β with diminished glycemic control in subjects with diabetes. That study also provided evidence that systemic levels of triglycerides may be associated with elevated GCF IL-1β. Losche et al. (Losche, W. et al., Plasma lipid and blood glucose levels in patients with destructive periodontal disease. J. Clin. Periodontol, 27:537-541, 2000) also found elevated circulating lipid levels in subjects with periodontitis, which is consistent with the findings of Cutler et al. (Cutler, C. W. et al., Heightened gingival inflammation and attachment loss in type 2 diabetics with hyperlipidemia. J. Periodontol, 70:1313-1321, 1999). The present study did not examine the role of hyperlipidemia in GCF IL-1β levels; hence, the inventor could not evaluate the relative contribution of lipids in the multivariate model. Certainly larger studies are needed to address both the role of hyperlipidemia and hyperglycemia in gingival inflammation.

A hyperresponsive monocytic trait has been pro-posed by Salvi et al. (Salvi, G. E. et al., Inflammatory mediator response as a potential risk marker for periodontal diseases in insulin-dependent diabetes mellitus patients. J. Periodontol, 68:127-135, 1997; Salvi, G. E. et al., PGE2, IL-1β, and TNF-a responses in diabetics as modifiers of periodontal disease expression. *Ann. Periodontol,* 3:40-50, 1998) as an explanation for elevated cytokine levels found in type 1 diabetes patients. This hypothesis holds that a heightened inflammatory response, either as a result of gene polymorphism or hyperglycemia, causes a heightened monocyte release of inflammatory mediators. While it is possible that genetic polymorphisms in the production of proinflammatory cytokines contribute to diabetes-related periodontitis, to the inventor's knowledge no specific gene or genotype has been tested thus far. This study supports the concept that hyperglycemia influences elevated inflammatory mediators in GCF and does not rule out the possibility that a hyperresponsive monocyte trait is also present in type 2 diabetes patients.

An alternative hypothesis to the hyperresponsive monocytic trait theory is that elevated glucose levels may directly or indirectly lead to a heightened inflammatory response. Acute and chronic hyperglycemic models have been studied. Ex vivo stimulation of monocytes of human volunteers with solutions high in glucose resulted in increased tumor necrosis factor-a (TNF-α) and IL-6 (Morohoshi, M. et al., Glucose-dependent interleukin 6 and tumor necrosis factor production by human peripheral blood monocytes in vitro. *Diabetes,* 45:954-959, 1996). A recent human experimental study by Esposito et al. (Esposito, K. et al., Inflammatory cytokine concentrations are acutely increased by hyperglycemia in humans: Role of oxidative stress. *Circulation,* 106:2067-2072, 2002) demonstrated that circulating levels of TNF-α, and IL-6 became elevated acutely in response to a bolus of glucose in healthy and impaired glucose tolerance individuals. These researchers concluded that acute hyperglycemia raised circulating cytokines through an oxidative mechanism, since an infusion of the antioxidant glutathione resulted in no increase of cytokines following a glucose bolus administration. Hence, there is evidence for increased inflammatory mediator activity in the presence of acute hyperglycemia. In this study, random glucose was significantly associated with elevated GCF IL-1β. This finding may indicate that the hyperglycemic excursions in serum glucose frequently encountered by patients with diabetes may contribute acutely to GCF IL-1β levels.

The effects of chronic hyperglycemia on inflammatory mediators are also well documented. Clinical and animal studies have shown that chronic hyperglycemia is associated with increased inflammatory mediator levels (Brownlee, M. et al., Advanced glycosylation end products in tissue and the biochemical basis of diabetic complications, *N. Engl. J. Med.,* 318:1315-1321, 1988; Yan, S. D. et al., Enhanced cellular oxidant stress by the interaction of advanced glycation end products with their receptors/binding proteins. *J. Biol. Chem.,* 269:9889-9897, 1994; Schmidt, A. M. et al., The multiligand receptor RAGE as a progression factor amplifying immune and inflammatory responses. *Diabetes,* 50:2792-2808, 2001; Schmidt, A. M. et al., Elevated plasma levels of vascular cell adhesion molecule-1 (VCAM-1) in diabetic patients with microalbuminuria: A marker of vascular dysfunction and progressive vascular disease. *Br. J. Haematol,* 92:747-750, 1996; Vlassara, H. et al., Cachectin/TNF and IL-1 induced by glucose-modified proteins: Role in normal tissue remodeling. *Science,* 240:1546-1548, 1988; Schmidt, A. M. et al., Advanced glycation endproducts (AGEs) induce oxidant stress in the gingiva: A potential mechanism underlying accelerated periodontal disease associated with diabetes. *J. Periodontal Res.,* 31:508-515, 1996; Schmidt, A. M. et al., Cellular receptors for advanced glycation end products. Implications for induction of oxidant stress and cellular dysfunction in the pathogenesis of vascular lesions. *Arterioscler. Thromb.,* 14:1521-1528, 1994; Schmidt, A. M. et al., RAGE: A novel cellular receptor for advanced glycation end products. *Diabetes,* 45(Suppl. 3):S77-S80, 1996). A mechanism to account for this finding involves the non-enzymatic glycation of tissue proteins and the production of advanced glycation end products (AGEs) (Brownlee, M. et al., Advanced glycosylation end products in tissue and the biochemical basis of diabetic complications, *N. Engl. J. Med.,* 318:1315-1321, 1988). Hyperglycemia results in reversible and irreversible change to the host including formation of AGEs. Receptors for AGEs (RAGE) have been identified. AGE formation and AGE-RAGE interaction at the cell surface of endothelial cells and mononuclear phagocytes have been shown to generate reactive oxygen intermediates (Yan, S. D. et al., Enhanced cellular oxidant stress by the interaction of advanced glycation end products with their receptors/binding proteins. *J. Biol. Chem.,* 269:9889-9897, 1994) and enhance the expression of proinflammatory cytokines (Schmidt, A. M. et al., The multiligand receptor RAGE as a progression factor amplifying immune and inflammatory responses. *Diabetes,* 50:2792-2808, 2001) through a mechanism involving the nuclear transcription factor kappa B (NF-κB). AGE-RAGE interactions have been shown in vitro to upregulate NF-κB associated gene products (Yan, S. D. et al., Enhanced cellular oxidant stress by the interaction of advanced glycation end products with their receptors/binding proteins. *J. Biol. Chem.,* 269:9889-9897, 1994) which include vascular cell adhesion molecule (Schmidt, A. M. et al., Elevated plasma levels of vascular cell adhesion molecule-1 (VCAM-1) in diabetic patients with microalbuminuria: A marker of vascular dysfunction and progressive vascular disease. *Br. J. Haematol,* 92:747-750, 1996) and proinflammatory cytokines (Vlassara, H. et al., Cachectin/TNF and IL-1 induced by glucose-modified proteins: Role in normal tissue remodeling. *Science,* 240:1546-1548, 1988). RAGE is present in the gingival tissues and has been linked to oxidative stress (Schmidt, A. M. et al., Advanced glycation endproducts (AGEs) induce oxidant stress in the gingiva: A potential mechanism underlying accelerated periodontal disease associated with diabetes. *J. Periodontal Res.,* 31:508-515, 1996). The inventor reasons that if AGE-RAGE interactions are taking place within the gingival tissues, then a heightened cytokine response should differentiate patients with more pronounced hyperglycemia. Since RAGE receptors are present on mononuclear phagocytes (Schmidt, A. M. et al., Cellular receptors for advanced glycation end products. Implications for induction of oxidant stress and cellular dysfunction in the pathogenesis of vascular lesions. *Arterioscler. Thromb.,* 14:1521-1528, 1994), AGE-RAGE interactions in the tissues of diabetic subjects may account for a heightened inflammatory response (Schmidt, A. M. et al., RAGE: A novel cellular receptor for advanced glycation end products. *Diabetes,* 45(Suppl. 3):S77-S80, 1996). Hence, the finding that GCF IL-1β is increased in subjects with worse glycemic control is not unexpected. This study found that elevated HbA1c was associated with GCF IL-1β, which is consistent with a role for chronic hyperglycemia in the production of gingival inflammation. Since chronic hyperglycemia can lead to the non-enzymatic glycation of tissue proteins, glycation of tissue protein may contribute to pathologic vascular change and subsequent tissue damage (Schmidt, A. M. et al., Cellular receptors for advanced glycation end products. Implications for induction of oxidant stress and cellular dysfunction in the pathogenesis of vascular lesions. *Arterioscler. Thromb.,* 14:1521-1528, 1994). While not an AGE itself, HbA1c is a measure of hemoglobin glycation, and as such is a measure of chronic hyperglycemia.

Elevated IL-1β represents, in part, a plausible explanation for the increased incidence and severity of periodontal disease in patients with diabetes. The relationship of poor glycemic control to GCF IL-1β requires further study in light of the current findings. Other cytokines are likely to play a role in this regard as well. One limitation of the present study is that only small amounts of GCF can be collected at one visit. The small volume of GCF sample limits the number of inflammatory mediators that can be reliably measured. Clearly there is a need for GCF testing technologies which could measure many inflammatory mediators simultaneously from such very small fluid volumes. Another limitation of this study is that testing was not done for genetic polymorphisms. Future studies should consider genetic variation in IL-1β, and other inflammatory mediator expression.

The present study was designed to sample predetermined anatomic locations within the periodontium rather than the most inflamed or deepest sites. Shallow, medium, and deep probing depths were encountered in this study so that sites with clinically different characteristics could be compared. Sampling only inflamed or deepest sites may give an inaccurate profile of inflammatory mediators since probing depth and clinical inflammation are strongly associated with IL-1β (Engebretson, S. P et al., GCF IL-1beta profiles in periodontal disease. *J. Clin. Periodontol,* 29:48-53, 2002; Oringer, R. J. et al., Effect of locally delivered minocycline microspheres on markers of bone resorption. *J. Periodontol,* 73:835-842, 2002). Any description of inflammatory mediators in the GCF from diseased periodontium should, therefore, consider the probing depth of the sampled site.

Also, the current finding of elevated GCF IL-1β in diabetic subjects with poor glycemic control raises the possibility of the converse; namely, that local gingival inflammation may adversely influence the glycemic control of patients with diabetes. An excellent review of the complex association between inflammation, hyperlipidemia, and hyperglycemia was recently published (Fernandez-Real, J. M. et al., Insulin resistance and chronic cardiovascular inflammatory syndrome, *Endocr. Rev.,* 24:278-301, 2003). Whether inflammation precedes clinical diabetes is an intriguing proposition. This question has been addressed in at least one large cohort stud (Duncan, B. B. et al., Factor VIII and other hemostasis variables are related to incident diabetes in adults. The Atherosclerosis Risk in Communities (ARIC) Study. *Diabetes Care,* 22:767-772, 1999). Results reported by the Atherosclerosis Risk in Communities Study investigators indicate that baseline levels of inflammatory mediators in serum were significant predictors of incident diabetes at the 7-year follow-up (Duncan, B. B. et al., Factor VIII and other hemostasis variables are related to incident diabetes in adults. The Atherosclerosis Risk in Communities (ARIC) Study. *Diabetes Care,* 22:767-772, 1999). This association was found even after adjusting for baseline fasting glucose levels. The authors concluded that inflammation may precede development of diabetes. Their data support the hypothesis that host inflammation may contribute to hyperglycemia. It is conceivable that elevated GCF IL-1β may contribute to hyperglycemia. At least one human study has examined the issue of whether chronic periodontitis influences circulating lipid and glucose levels (Losche, W. et al., Plasma lipid and blood glucose levels in patients with destructive periodontal disease. *J. Clin. Periodontol,* 27:537-541, 2000). Losche et al. (Losche, W. et al., Plasma lipid and blood glucose levels in patients with destructive periodontal disease. *J. Clin. Periodontol,* 27:537-541, 2000) reported increased levels of serum glucose in non-diabetic subjects with periodontitis compared with age- and gender-matched non-diabetic subjects without periodontitis. The question of whether gingival inflammation contributes to hyperglycemia in patients with diabetes needs to be addressed in future interventional studies.

In summary, these data indicate a significant increase in GCF inflammatory mediator levels among patients with type 2 diabetes and poor glycemic control. Hyperglycemia may, in part, explain the increased incidence and severity of periodontal disease among type 2 diabetes patients.

Example 8

Plasma Levels of Tumor Necrosis Factor Alpha (TNF-α) in Patients with Chronic Periodontitis and Type 2 Diabetes Studies suggest that elevated circulating tumor necrosis factor-alpha (TNF-alpha) may contribute to insulin resistance in patients with type 2 diabetes. The source of plasma TNF has been thought to be adipocytes associated with obesity, but inflammation and infection result in TNF-alpha production as well.

Methods. The inventor studied 45 patients with type 2 diabetes and chronic periodontitis. He evaluated the relationship of plasma TNF-alpha levels with clinical measures of periodontal disease, gingival crevicular fluid interleukin-1β (IL-1β), serum glucose, and glycated hemoglobin (HbA1c). TNF-alpha levels were measured using a high sensitivity enzyme-linked immunosorbent assay.

Results. Patients with severe periodontitis had significantly higher TNF-alpha levels than subjects with mild periodontal disease ($P=0.012$). TNF-alpha showed a significant positive correlation with attachment loss ($r=0.395$, $P<0.009$) and GCF IL-1β($r=0.330$, $P=0.035$), but not probing depth ($r=0.276$, $P=0.07$), bleeding on probing ($r=0.296$, $P=0.053$), plaque index ($r=0.216$, $P=0.173$), serum glucose, HbA1c ($r=0.103$, $P=0.50$), or body mass index ($r=0.077$, $P=0.62$).

Conclusion. These results demonstrate that periodontitis contributes to circulating TNF-alpha levels and hence play a role in insulin resistance associated with type 2 diabetes.

Example 9

Plasma TNF and Endotoxin in Diabetic and Non-Diabetic Periodontitis Subjects

Studies suggest that patients with type 2 diabetes have elevated circulating tumor necrosis factor alpha (TNF) levels compared with non-diabetic individuals. Periodontitis may contribute to elevated circulating endotoxin levels. The purpose of this study was to compare TNF and endotoxin levels in periodontal disease patients with and without type 2 diabetes.

Methods. The inventors studied 45 subjects with type 2 diabetes and 28 subjects of similar periodontal disease severity but without diabetes. Attachment level (AL), probing depth (PD), bleeding on probing (BOP), and plaque index (PI), were measured. An end-point *limulus* amebocyte lysate assay, and a high sensitivity ELISA were used to determine plasma endotoxin and TNF respectively.

Results. Subjects with detectable endotoxin ($p=0.04$), or above median TNF ($p=0.04$), had significantly greater mean AL. When diabetic and non-diabetic subjects were compared TNF and endotoxin levels were not significantly different. TNF levels showed a significant positive correlation with endotoxin levels in diabetic (p=0.03, r=0.33) but not non-diabetic subjects (p=. 17, r=0.286). Mean AL but not mean PD, BOP, or PI showed a significant positive correlation with TNF in diabetic subjects (p=0.01, r=0.395). For non-diabetic subjects there was no significant correlation between either TNF or endotoxin and periodontal clinical parameters. In a multivariate model, adjusting for age, gender, diabetic status, detectable endotoxin, and periodontal status, AL>4 mm (OR, 4.3; 95% CI, 1.25 to 14.8) and detectable endotoxin (OR, 4.2; 95% CI, 1.20 to 14.5) but not diabetes status, were significant independent predictors of elevated (highest quartile) plasma TNF.

Conclusion. These results indicate that chronic periodontitis is a significant independent predictor of circulating TNF levels regardless of diabetes status. These data further suggest that periodontal disease measures are an important component of overall assessment of patient inflammation.

Example 10

Analysis of Circulating TNF

The effect of decreasing the level of IL-1β in GCF on the level of circulating TNF is further examined.

Subjects are selected and divided into different groups as described in Examples 1 and 2. An oral rinse containing 0.1% Ketorolac was administered twice daily for 6 months to reduce the level of IL-1β in GCF in the subjects (see, Cavanaugh et al., Coordinate production of PGE2 and IL-1 beta in the gingival crevicular fluid of adults with periodontitis: its relationship to alveolar bone loss and disruption by twice daily treatment with ketorolac tromethamine oral rinse. *J. Periodontal Res.* 33:75-82, 1998). GCF samples are collected following the procedures of example 3 and the level of IL-1β in GCF is determined as described in example 5. Circulating TNF level is determined by measuring blood TNF level using the TNF alpha immunoassay kit (Assay Designs Inc., Ann Arbor, Mich.) following the manufacturer's instructions. Reducing the level of IL-1β in GCF by Ketorolac will result in a significant reduction in the level of serum TNF.

Example 11

Metabolic Control

The effect of decreasing the level of IL-1β in GCF on metabolic control is also examined.

The study is performed as described in example 8. HbA1c levels and serum glucose levels, which are used as indicators of metabolic control, are measured as described in example 6. Ketorolac treatment is likely to decrease the levels of circulating TNF through reducing the levels of IL-1β in GCF, which then causes the decline of HbA1c levels and serum glucose levels in the subjects.

While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A method for facilitating metabolic control in a subject, comprising decreasing the level of IL-1β in GCF of the subject by administering to the subject an anti-inflammatory ketorolac oral rinse, wherein the subject has type 2 diabetes and periodontitis.

2. The method of claim 1, wherein metabolic control is facilitated in the subject by a decrease in the level of circulating TNF in the subject.

3. The method of claim 1, wherein the metabolic control in the subject is glucose control.

4. The method of claim 1, wherein the subject further has hyperglycemia.

5. The method of claim 1, further comprising performing a scaling and root planing (SRP) operation on the subject.

6. A method of use of an anti-inflammatory agent in a method for facilitating metabolic control in a subject by decreasing the level of IL-1β in GCF of the subject by administering to the subject an anti-inflammatory ketorolac oral rinse, wherein the subject has type 2 diabetes and periodontitis.

* * * * *